United States Patent
Garcia-Garcia et al.

(10) Patent No.: US 10,849,866 B2
(45) Date of Patent: Dec. 1, 2020

(54) METHODS FOR INHIBITING CONVERSION OF CHOLINE TO TRIMETHYLAMINE (TMA)

(71) Applicants: The Procter & Gamble Company, Cincinnati, OH (US); The Cleveland Clinic, Cleveland, OH (US)

(72) Inventors: Jose Carlos Garcia-Garcia, Cincinnati, OH (US); George Franklin Gerberick, Cincinnati, OH (US); Stanley Leon Hazen, Pepper Pike, OH (US); Xiaodong Gu, Cleveland, OH (US)

(73) Assignees: The Procter & Gamble Company, Cincinnati, OH (US); The Cleveland Clinic Foundation, Cleveland, OH (US)

( * ) Notice: Subject to any disclaimer, the term of this patent is extended or adjusted under 35 U.S.C. 154(b) by 105 days.

(21) Appl. No.: 16/149,938

(22) Filed: Oct. 2, 2018

(65) Prior Publication Data
US 2019/0099390 A1    Apr. 4, 2019

Related U.S. Application Data

(60) Provisional application No. 62/567,010, filed on Oct. 2, 2017.

(51) Int. Cl.
| | |
|---|---|
| *A61K 31/14* | (2006.01) |
| *A61K 45/06* | (2006.01) |
| *A61P 3/00* | (2006.01) |
| *A61P 43/00* | (2006.01) |

(52) U.S. Cl.
CPC ............ *A61K 31/14* (2013.01); *A61K 45/06* (2013.01); *A61P 3/00* (2018.01); *A61P 43/00* (2018.01)

(58) Field of Classification Search
None
See application file for complete search history.

(56) References Cited

U.S. PATENT DOCUMENTS

| | | | |
|---|---|---|---|
| 3,644,531 A | 2/1972 | Kishida | |
| 3,651,222 A | 3/1972 | Gee | |
| 9,168,233 B2 | 10/2015 | Hazen | |
| 2013/0345171 A1 | 12/2013 | Hazen et al. | |
| 2017/0151208 A1 | 6/2017 | Hazen et al. | |
| 2017/0151250 A1 | 6/2017 | Hazen et al. | |
| 2017/0152222 A1 | 6/2017 | Garcia-Garcia et al. | |
| 2018/0000754 A1 | 1/2018 | Hazen et al. | |

FOREIGN PATENT DOCUMENTS

| | | | |
|---|---|---|---|
| EP | 0555058 A1 | 8/1993 | |
| FR | 1559102 A | 3/1969 | |
| GB | 1179907 A | 2/1970 | |
| GB | 1424147 A | 2/1976 | |
| JP | 2007210982 A | 8/2007 | |

OTHER PUBLICATIONS

U.S. Appl. No. 16/149,882, filed Oct. 2, 2018, Jose Carlos (NMN) Garcia-Garcia et al.
U.S. Appl. No. 16/149,913, filed Oct. 2, 2018, Jose Carlos (NMN) Garcia-Garcia et al.
Hiroshi Yamazaki et al.; "Effects of the Dietary Supplements, Activated Charcoal and Copper Chlorophyllin, On Urinary Excretion of Trimethylamine in Japanese Trimethylaminuria Patients" Life Sciences (2004) 74: 2739-2747.
Zeneng Wang et al.; "Gut Florametabolism of Phosphatidylcholine Promotes Cardiovascular Disease", Nature (2011), 472: 57-63.
Smaranda Craciun and Emily P. Balskus; "Microbial Conversion of Choline to Trimethylamine Requires a Glycyl Radical Enzyme" ; Proc. Natl. Acad. Sci. (2012), 109: 21307-21312.
W.H. Wilson Tang,et al.; "Intestinal Microbial Metabolism of Phosphatidylcholine and Cardiovascular Risk", NEJM (2013) 368: 1575-1584.
Smaranda Craciun, Jonathan A. Marks, and Emily P. Balskus; "Characterization of Choline Trimethylamine-Lyase Expands the Chemistry of Glycyl Radical Enzymes" (2014) American Chemical Society Chemical Biology 9: 1408-1413.
Ana Martínez-Del Campo, et al.; "Characterization and Detection of a Widely Distributed Gene Cluster That Predicts Anaerobic Choline Utilization by Human Gut Bacteria"; (2015) mBio 6(2):e00042-15.
International Search Report and Written Opinion dated Jan. 8, 2019, U.S. Appl. No. 16/149,938, 11 pgs.
International Search Report and Written Opinion dated Jan. 9, 2019, U.S. Appl. No. 16/149,882, 13 pgs.
International Search Report and Written Opinion dated Jan. 9, 2019, U.S. Appl. No. 16/149,913, 13 pgs.
Kaspars Tars et al., "Targeting Carnitine Biosysthesis: Discovery of New Inhibitors against [gamma]-Butyrobetaine Hydroxylase", Journal of Medical Chemistry, vol. 57, No. 6, Mar. 27, 2014, pp. 2213-2623.
Mistry et al. "Neurochemistry of aging. Toxins for an animal model of Alzheimer's Disease", Journal of medicinal chemistry, Mar. 1, 1986, pp. 376-380, XP55531027.
Rozengart et al., "A Comparative Study of Sulfonium Reversible Inhibitors of Cholinesterases of Various Animals", Doklady Biochemistry and Biophysics, vol. 395, Jan. 1, 2004, pp. 61-64.
Beitnere et al, "Mildronate Improves Cognition and Reduces Amyloid Beta Pathology in Transgenic Alzheimer's Disease Mice", Journal Neurosci Res., Mar. 2014, 92(3), pp. 338-346.
Du et al, "Dietary eicosapentaenoic acid supplementation accentuates hepatic triglyceride accumulation in mice with impaired fatty acid oxidation capacity," Biochimica et Biophysica Acta 1831 (2013), pp. 291-299
Office Action dated May 16, 2019, U.S. Appl. No. 16/149,913.
Office Action dated Sep. 11, 2019, U.S. Appl. No. 16/149,882.

*Primary Examiner* — Dennis Heyer
(74) *Attorney, Agent, or Firm* — James E Oehlenschlager

(57) ABSTRACT

A method of inhibiting the conversion of choline to trimethylamine (TMA) and lowering TMAO in an individual by providing a composition comprising a compound set forth in Formula (I):

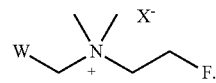

Formula (I)

8 Claims, No Drawings

METHODS FOR INHIBITING CONVERSION OF CHOLINE TO TRIMETHYLAMINE (TMA)

FIELD OF THE INVENTION

The invention generally relates to materials and methods for inhibiting trimethylamine production in an individual.

BACKGROUND

Trimethylamine (TMA) and its derivative trimethylamine N-oxide (TMAO) are metabolites linked to disorders such as kidney disease, diabetes mellitus, obesity, trimethylaminuria, and cardiovascular disease (CVD). TMA is produced in the gut by bacteria which are capable of converting substrates including but not limited to choline, to TMA. There is an unmet need for compounds which inhibit the production of TMA by bacteria.

CVD is a general term encompassing a range of conditions affecting the heart and blood vessels, including atherosclerosis, coronary heart disease, cerebrovascular disease, heart failure, cardiomyopathy, atherothrombotic disease, aorto-iliac disease, and peripheral vascular disease. CVD is generally associated with conditions that involve narrowed, blocked, aneurysmal or dissection of one or more blood vessels, or thrombosis (blood clot formation). Complications associated with CVD include, but are not limited to, myocardial infarction, stroke, angina pectoris, acute coronary syndrome, transient ischemic attacks, congestive heart failure, aortic aneurysm, atrial fibrillation or flutter, ventricular arrhythmias, cardiac conduction abnormalities, need for revascularization and death. Revascularization can include but is not limited to angioplasty, stenting, coronary artery bypass grafting, repair or replacement of vascular shunt or access such as an arteriovenous fistula. Complications associated with atherothrombotic disease include, but are not limited to, myocardial infarction, stroke, pulmonary embolism, deep venous thrombosis. According to the World Health Organization, CVDs are the leading cause of death globally, with over 75% of deaths occurring in low- and middle-income countries. World Health Organization Fact Sheet No. 317, updated January 2015. The World Health Organization projects that diabetes will be the seventh leading cause of death in 2030. World Health Organization Fact Sheet No. 312, updated January 2015. Prevention and management of conditions associated with TMA and TMAO, including CVD and diabetes, is a major public health concern.

SUMMARY OF THE INVENTION

The disclosure is based, at least in part, on the discovery that compounds of Formula (I) inhibit choline metabolism by gut microbiota resulting in reduction in the formation of trimethylamine (TMA). The disclosure provides compositions and methods for, e.g., inhibiting the conversion of choline to TMA in vitro and in vivo, for improving or maintaining cardiovascular, cerebrovascular, or peripherovascular health, and for improving or preventing a condition associated with TMA and TMAO. In certain aspects, the invention provides one or more methods of inhibiting the conversion of choline to TMA in an individual.

In certain aspects, the invention provides one or more methods of reducing the production of TMAO comprising inhibiting the conversion of choline to TMA by a bacterium, by providing one or more compounds as set forth in Formula (I). The invention provides a method of inhibiting the conversion of choline to TMA in an individual. The method comprises administering to the individual a composition comprising a compound set forth in Formula (I):

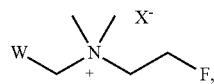

Formula (I)

wherein:
W is selected from F, Cl, Br or I; X⁻ is a pharmaceutically acceptable anion, and salts or solvates thereof.

The compound of Formula (I) can be administered in an amount effective to inhibit conversion of choline to TMA and TMAO in the individual.

The invention further provides a method of improving or maintaining cardiovascular health. A method may comprise administering to the individual a composition comprising a compound as set forth in Formula (I), as described herein in an amount that improves or maintains cardiovascular health. The invention also provides a method of improving a condition associated with the conversion of choline to trimethylamine (TMA) in an individual. The method comprises administering to the individual a composition comprising a compound as set forth in Formula (I), as described herein in an amount effective to improve the condition. In some embodiments, the condition may be trimethylaminuria, reduced or impaired kidney function, kidney disease, chronic kidney disease (CKD), end-stage renal disease (ESRD), diabetes mellitus, obesity, or cardiovascular disease, such as angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, peripheral artery disease (PAD), or stroke. In some embodiments, the condition is adverse ventricular remodeling, ventricular systolic dysfunction, ventricular diastolic dysfunction, cardiac dysfunction, ventricular arrhythmia, or cardiovascular disease or atherosclerosis due to oral biofilm formation and periodontal disease.

The invention further provides the compounds of Formula (I) for use in inhibiting the conversion of choline to TMA in vivo or in vitro, for improving or maintaining cardiovascular health, and for improving a condition associated with the conversion of choline to TMA; and use of the compounds of Formula (I) for inhibiting the conversion of choline to TMA in vivo or in vitro, for improving or maintaining cardiovascular health, and for improving a condition associated with the conversion of choline to TMA.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus. In certain aspects, the invention may be described as related to a substrate, for example choline, and may also relate to metabolites or precursors of said substrate, for example precursors or metabolites of choline such as lecithin or glycerophosphocholine. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise, for example X or Y, means X or Y or both. If aspects of the invention are described as "comprising" a feature, embodiments also are contemplated "consisting of" or "consisting essentially of" the feature.

DETAILED DESCRIPTION OF THE INVENTION

The components of the present compositions are described in the following paragraphs.

The present invention provides one or more methods of reducing the production of TMA comprising: inhibiting the conversion of choline to TMA by a bacterium using a composition comprising a compound set forth in Formula (I). The present invention also provides synthesis methods to produce a series of selected haloalkyl amine derivatives, as exemplified in Formula (I). Such compounds may be used to inhibit the conversion of choline to TMA in vivo or in vitro, or inhibit the production of TMA by bacteria. The compounds of Formula (I) may be administered to an individual in an amount effective to inhibit the production of TMA and TMAO by bacteria in the gut of an individual, for example from substrates including but not limited to choline.

TMA synthesized by bacteria resident in the gut of mammals is oxidized in the liver to trimethylamine N-oxide (TMAO, TMANO). Exemplary precursors of TMA include choline, betaine, phosphatidylcholine, phosphocholine, glycerophosphocholine, carnitine, L-carnitine, TMAO, sphingomyelin, and lecithin, many of which are derived from dietary sources such as, for example, whole eggs and beef liver. These sources may act as substrates for bacteria that can metabolize them to TMA. Without wishing to be bound to a particular mechanism or biochemical pathway, the anaerobic conversion of choline to TMA is facilitated by a glycyl radical enzyme homologue, choline trimethylamine-lyase (CutC). Craciun et al., Proc. Natl. Acad. Sci. (2012), 109: 21307-21312. The reduction of choline conversion to TMA by bacteria in the gut of an individual leads to a reduction in TMA absorption from the gut, leading to a subsequent reduction in plasma TMAO following oxidation of TMA to TMAO by the flavin monooxygenase 3 (FMO3) enzyme in the liver. Wang et al., Nature (2011), 472: 57-63. Lower plasma TMAO levels are related to a lower incidence of major cardiovascular events in humans. Tang et al., NEJM (2013) 368: 1575-1584. The conversion of choline to TMA may be mediated by one species of bacteria or comprise a multi-step process involving two, three or more species of bacteria.

As described previously, the present invention is based, at least in part, on the discovery that compounds of Formula (I) interfere with choline metabolism by gut microbiota resulting in reduction in the formation of TMA and trimethylamine N-oxide (TMAO). The disclosure provides compositions and methods that for example inhibit the conversion of choline to TMA in vitro and in vivo, improve or maintain cardiovascular, cerebrovascular, and peripherovascular health, and improve or prevent a condition associated with increased TMA and TMAO. Other conditions associated with increased levels of TMA may include production of TMA by bacteria in the vagina leading to vaginal odor, or production of TMA by bacteria on the body leading to body odor, or production of TMA by bacteria in the mouth leading to bad breath or oral care biofilm development, or during pregnancy where the third trimester and post-partum period are associated with an increased risk of thrombosis, thus lowering TMA and TMAO levels may reduce this risk. The disclosure additionally provides compositions and methods to increase the availability of choline in the gut of an individual with a condition where increased choline availability would be beneficial, by inhibiting choline catabolism. One such condition is during pregnancy and the post-partum period where increased choline availability in the gut of the mother may promote brain development for the fetus and newborn.

Conversion of choline to TMA by gut bacteria has been attributed to the glycyl radical enzyme homologue, choline trimethylamine-lyase CutC. Craciun et al. (2014) ACS Chem Biol 9: 1408-1413. It has been described that not all gut microbes contain the gene cluster including CutC. Martinez-del Campo et al. (2015) mBio 6(2):e00042-15. doi: 10.1128/mBio.00042-15. The cut gene cluster contains a set of genes encoding the glycyl radicle enzyme CutC, and a glycyl radicle activating protein CutD, cutC/D gene cluster. Craciun et al. (2012) PNAS 109:21307-21312.

In contrast, most sequenced bacteria convert choline to glycine betaine (GB, or trimethylglycine) which primarily acts as an osmoprotectant. Additionally, some bacteria can convert choline to GB and then to glycine, which may be used as a source of carbon and nitrogen. Wargo (2013) Appl. Environ. Microbiol. 79:2112-2120. *Pseudomonas aeruginosa* is one such species of bacteria that can convert choline to glycine via GB, dimethyl glycine (DMG) and sarcosine.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

The components of the present compositions are described in the following paragraphs.

As used herein, "dose" refers to a volume of medication, such as liquid medication or oral dosage unit, containing an amount of a drug active suitable for administration on a single occasion, according to sound medical practice. A dose can be orally administered. In one example, a dose can be a liquid medication and can be about 30 mL, in another example about 25 mL, in another example about 20 mL, in another example about 15 mL, and in another example about 10 mL, and in another example about 5 mL. In another example, a dose of liquid medication can be from about 5 mL to about 75 mL, in another example from about 10 mL to about 60 mL, in another example from about 15 mL to about 50 mL, in another example from about 25 mL to about 40 mL, and in another example from about 28 mL to about 35 mL. In another example, the dose can be a solid dosage form and can be from about 25 mg to about 5 g, in another example from about 100 mg to about 3 g, in another example from about 250 mg to about 2 g, in another example from about 500 mg to about 1.6 g, and in another example from about 750 mg to about 1 g. In addition, a dose may be a solid dosage form wherein one dose is about 3 g or a dose can be about 1.6 g. The concentration of active ingredients can be adjusted to provide the proper doses of actives given the liquid or solid dose size. In certain embodiments, a dose can be administered about every 4 hours, about every 6 hours, about every 8 hours, about every 12 hours, or about every 24 hours.

As used herein, "medication" refers to compositions comprising a compound of Formula (I), such as pharmaceuticals, including prescription medications, over-the-counter medications, behind-the-counter medications and combinations thereof. In some examples, a medication can be a dietary supplement which can contain vitamins, minerals, and supplements (VMS) including supplements or ingredients such as botanicals.

Medication compositions can be in any suitable form including liquid compositions and solid oral dosage forms. Non limiting examples of liquid compositions can include syrups, beverages, supplemental water, foam compositions, gel compositions, particles suspended in a liquid formulation, a solid in a gelatin or foam, saline wash and combinations thereof. Non-limiting examples of solid oral dosage forms can include tablets, capsules, caplets, sachets, sublingual dosage forms, buccal dosage forms, soft gels, and other liquid filled capsules, dissolvable dosage forms including dissolvable strips, films, gums including a center filled gum, gummies including a center filled gummy, lozenges, center filled tablets, powder, granules, pellets, microspheres, nanospheres, beads, or nonpareils, and combinations thereof. Tablets can include compressed tablets, chewable tablets, dissolvable tablets, and the like. In some examples, the medication can be applied to the skin, in an ointment such as a petroleum jelly based ointment. In some examples the medication may be provided in a delivery device. In other examples, the medication can be inhaled, such as a nose spray or inhaler. In still other examples, the medication can be in a drink, such as a warm beverage. In further examples, the medication can contain a pharmaceutical active.

The medications can be in a form that is directly deliverable to the mouth, throat, or skin. In some embodiments, the medication compositions can be delivered by a delivery device selected from droppers, pump, sprayers, liquid dropper, saline wash delivered via nasal passageway, cup, bottle, canister, pressurized sprayers, atomizers, air inhalation devices, squeezable sachets, power shots, blister cards, and other packaging and equipment, and combinations thereof. The sprayer, atomizer, and air inhalation devices can be associated with a battery or electric power source.

As used herein the term "individual" includes both humans and other types of mammals sharing the TMAO pathway, such as domesticated animals, including but not limited to, domestic dogs (canines), cats (feline), horses, cows, ferrets, rabbits, pigs, rats, mice, gerbils, hamsters, horses, and the like.

A wide variety of individuals may wish to reduce the level of TMA produced by bacteria in their digestive tract. For example, individuals diagnosed with cardiovascular disease may be directed by a physician to take prescription drugs or effect lifestyle changes to modulate blood cholesterol levels to reduce the risk of serious cardiovascular events. Other individuals not previously diagnosed with cardiovascular disease but who wish to improve or maintain cardiovascular health may also wish to reduce the level of TMA produced by digestive tract bacteria. As described further herein, a reduction in TMA (and, by extension, TMAO) is achieved by the compositions described herein, which may include, for example, a dietary supplement comprising the compounds of Formula (I).

The disclosure includes, a method of inhibiting the conversion of choline to TMA, a method of improving cardiovascular health, and a method of improving a condition associated with conversion of choline to TMA comprising administering to the individual a composition comprising a compound of Formula (I). Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods or compounds described herein can be deleted, combined with, or substituted for, in whole or part, any other feature described herein.

Compounds

The methods of the present invention may comprise administering to the individual a composition comprising a compound set forth in Formula (I):

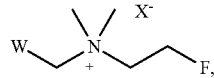

Formula (I)

wherein:

W is selected from F, Cl, Br or I; X⁻ is a pharmaceutically acceptable anion, and salts or solvates thereof.

In certain embodiments, the compound (as shown in TABLE 2 herein) may be selected from the group consisting of N-(chloromethyl)-2-fluoro-N,N-dimethylethan-1-aminium chloride, 2-fluoro-N-(iodomethyl)-N,N-dimethylethan-1-aminium chloride, (2-fluoroethyl)(fluoromethyl)dimethyl-14-azane chloride and N-(bromomethyl)-2-fluoro-N,N-dimethylethan-1-aminium chloride, and salts or solvates thereof.

In certain embodiments, the compound may be selected from the group consisting of N-(chloromethyl)-2-fluoro-N,N-dimethylethan-1-aminium, 2-fluoro-N-(iodomethyl)-N,N-dimethylethan-1-aminium, (2-fluoroethyl)(fluoromethyl)dimethyl-14-azane, N-(bromomethyl)-2-fluoro-N,N-dimethylethan-1-aminium, and a pharmaceutically acceptable anion and salts and solvates thereof.

The compound is administered in an amount effective to achieve the desired effect, e.g., inhibit conversion of choline to TMA, improve or maintain cardiovascular health, or improve a condition associated with conversion of choline to TMA.

The invention further provides for methods to synthesize selected haloalkyl amine derivatives as representatives of Formula (I). Such compound derivatives may also be used to inhibit the production of TMA by a bacterium or for inhibiting the conversion of choline to TMA in vivo or in vitro, by providing a composition comprising a composition as set forth in Formula (I).

Compounds of Formula (I) can be synthesized using the general Scheme 1, shown below.

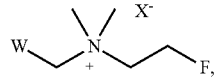

Formula (I)

wherein

X⁻ is a pharmaceutically acceptable anion and n is 1, 2 or 3 and including any acceptable salts or solvates thereof; comprising the steps of reacting Compound A:

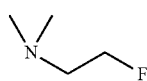

Compound A with a compound of structure B:

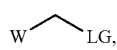

Structure B wherein LG is any suitable leaving group known to one skilled in the art, to form a compound of Formula (I); and any acceptable salts or solvates thereof.

X⁻ may be an anion capable of forming a salt with an ammonium group. In certain embodiments, X⁻ is a pharmaceutically acceptable anion selected from chloride, bromide, iodide, phosphate, and sulfate salts. Additional pharmaceutically acceptable acid addition salts include, for example, succinate, maleate, tartrate, citrate, glycolate, and trifluoromethanesulfonate or triflate, thus X⁻ may be selected from succinate, maleate, tartrate, citrate and glycolate. X⁻ is preferably a chloride, bromide, iodide, trifluoromethanesulfonate or triflate, salt form. When the compound of interest exists as a sulfoxide, then X⁻ is absent. When the compound of interest exists as a carboxylate, then X⁻ is absent.

"Alkyl" refers to straight chained and branched saturated hydrocarbon groups containing 1-30 carbon atoms (i.e., $C_1$-$C_{30}$), for example, 1-20 carbon atoms (i.e., $C_1$-$C_{20}$) or 1-10 carbon atoms (i.e., $C_1$-$C_{10}$). In various embodiments, the alkyl groups of Formula (I) are independently selected from $C_1$-$C_4$ alkyls, i.e., alkyl groups having a number of carbon atoms encompassing the entire range (i.e., 1 to about 4 carbon atoms), as well as all subgroups (e.g., 1-2, 1-3, 1-4, 2-3, 2-4, 3-4, 1, 2, 3, and 4 carbon atoms). Nonlimiting examples of alkyl groups include allyl, methyl, ethyl, n-propyl, isopropyl, n-butyl, sec-butyl (2-methylpropyl), t-butyl (1,1-dimethylethyl) and propargyl. Unless otherwise indicated, an alkyl group can be an unsubstituted alkyl group or a substituted alkyl group. Alkyl groups may also be substituted, for example, with one or more of hydroxy (OH), alkoxy, carboxy, cycloalkyl, heterocycloalkyl, and halo.

The term "heteroalkyl" is defined the same as alkyl except the hydrocarbon chain or branched chain contains one to three heteroatoms independently selected from oxygen, nitrogen or sulfur. The terms "heterocycloalkyl" or "heterocyclic" are defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, 4H-pyran, dihydrofuran, morpholine, thiophene, 1,4-dioxane, furan, pyridine, pyrrole, pyrrolidine, imidazole, pyrazole, triazole, thiazole, pyrazine, pyran, oxazole, oxazine, thiazine, pyrimidine, and the like. Cycloalkyl and heterocycloalkyl groups can be saturated or partially unsaturated ring systems optionally substituted with, for example, one to three groups, independently selected alkyl, alkenyl, OH, C(O)NH₂, NH₂, oxo (═O), aryl, haloalkyl, halo, and alkoxy. Heterocycloalkyl groups may also be further N-substituted with alkyl, hydroxyalkyl, alkoxyaryl, alkylenearyl, and alkyleneheteroaryl.

The terms "cycloalkyl" or "carbocyclic" refer to an aliphatic cyclic hydrocarbon group containing 3-8 carbon atoms (e.g., 3-5, 5-8, 3, 4, 5, 6, 7, or 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

The term "hydroxy" or "hydroxyl" refers to a "—OH" group. The term "amino" or "amine" refers to a —NH₂, or a —NH— group. "Amine" includes cyclic amines optionally substituted with one or more additional heteroatoms. The term "carboxy" or "carboxyl" refers to a "—COOH" group. The term "thiol" or "sulfhydryl" refers to a "—SH" group. The term "cyano" refers to a —C≡N group, also designated —CN.

A "substituted" alkyl, alkenyl, alkynyl, cycloalkyl, cycloalkenyl, aryl, heteroaryl, or alkoxyl, refers to an alkyl, alkenyl, alkynyl, cycloalkyl, cycloalkenyl, aryl, heteroaryl, or alkoxyl having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, amido, or sulfur. When a substituted alkyl group includes more than one non-hydrogen radical, the substituents can be bound to the same carbon or two or more different carbon atoms.

Physiologically acceptable salts of haloalkyl amine derivatives are contemplated and can be formed by reacting an ammonium compound with an alkylating agent containing a leaving group. Leaving groups commonly employed in alkylation reactions with sulfur are known in the art. Leaving groups such as, but not limited to those skilled in the art, include the halides (chlorine, bromine, iodine, etc.) and sulfonate esters of alcohols (tosylate, mesylate, cumenesulfonate, triflate, etc.). Physiologically accepted salts can be formed directly from the alkylation reaction of sulfur with an alkylating agent or can be prepared by an ion exchange process. Physiologically accepted salts include but are not limited to haloalkyl amine halides, phosphates, carboxylates, and sulfonates.

Salts, such as physiologically acceptable salts, of the disclosed compounds are contemplated and may be prepared by reacting the appropriate base or acid with a stoichiometric equivalent of the compound. Acids commonly employed to form physiologically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, cumenesulfonic acid, lactic acid, oxalic acid, para-bromophenylsulfonic acid, carbonic acid, succinic acid, citric acid, benzoic acid and acetic acid, as well as related inorganic and organic acids. Physiologically acceptable salts include sulfate, pyrosulfate, bisulfate, sulfite, bisulfite, phosphate, monohydrogenphosphate, dihydrogenphosphate, metaphosphate, pyrophosphate, chloride, bromide, iodide, trifluoromethanesulfonate or triflate, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, bitartrate, methanesulfonate, propanesulfonate, naphthalene-1-sulfonate, naphthalene-2-sulfonate, mandelate and other salts. Physiologically acceptable acid addition salts include, for example, those formed with mineral acids such as hydrochloric acid and hydrobromic acid and those formed with organic acids such as maleic acid.

Physiologically acceptable base addition salts may be formed with metals or amines, such as alkali and alkaline earth metals or organic amines. Physiologically acceptable salts of compounds may also be prepared with a physiologically acceptable cation. Physiologically acceptable cations that can be used are well known in the art and include alkaline, alkaline earth, ammonium and quaternary ammonium cations. Carbonates or hydrogen carbonates are also options in this regard. Examples of metals used as cations are sodium, potassium, magnesium, ammonium, calcium, ferric, and the like. Examples of amines that can be used include, but are not limited to, isopropylamine, histidine, N,N'-dibenzylethylenediamine, chloroprocaine, diethanolamine, dicyclohexylamine, ethylenediamine, N-methylglucamine, and procaine.

In a further embodiment, the compound is a stable isotope variant, for example wherein deuterium is substituted for one or more of the hydrogens.

In various embodiments, the compound of Formula (I) demonstrates an $IC_{50}$ of $1\times10^{-3}$ or less, $5\times10^{-3}$ or less, $1\times10^{-4}$ or less, $5\times10^{-4}$ or less, $1\times10^{-5}$ or less, $5\times10^{-5}$ or less, or $1\times10^{-6}$ or less, or $1\times10^{-7}$ or less, or $1\times10^{-8}$ or less, or $1\times10^{-9}$ or less, or $1\times10^{-10}$ or less or $1\times10^{-11}$ or less or $1\times10^{-12}$ or less, or between $1\times10^{-9}$ and $1\times10^{-3}$, or between $1\times10^{-12}$ and $1\times10^{-9}$, or between $1\times10^{-9}$ and $1\times10^{-6}$, or between $1\times10^{-8}$ and $1\times10^{-6}$, or between $1\times10^{-6}$ and $1\times10^{-3}$, between $1\times10^{-6}$ and $1\times10^{-4}$, between $1\times10^{-6}$ and $1\times10^{-5}$, between $1\times10^{-5}$ and $1\times10^{-3}$, or between $1\times10^{-4}$ and $1\times10^{-3}$, or between $1.7\times10^{-11}$ and $1\times10^{-7}$, (observed 50% inhibition of TMA (or TMAO) formation from choline; mol/L), in the assays described in EXAMPLE 2 or EXAMPLE 5. In various embodiments, the compound of Formula (I) demonstrates an $IC_{50}$ of between $1\times10^{-11}$ and $1\times10^{-7}$, or between $1\times10^{-8}$ to $1\times10^{-3}$, or between $1.2\times10^{-6}$ to $2\times10^{-3}$, or between $1\times10^{-6}$ to $1\times10^{-4}$ (observed 50% inhibition of TMA formation from choline; mol/L) as measured in the assays described in EXAMPLE 2 or EXAMPLE 5.

In various embodiments, the compound of Formula (I) demonstrates an $EC_{50}$ of $1\times10^{-3}$ or less, $5\times10^{-3}$ or less, $1\times10^{-4}$ or less, $5\times10^{-4}$ or less, $1\times10^{-5}$ or less, $5\times10^{-5}$ or less, or $1\times10^{-6}$ or less, or $1\times10^{-7}$ or less, or $1\times10^{-8}$ or less, or $1\times10^{-9}$ or less, or $1\times10^{-10}$ or less or $1\times10^{-11}$ or less or $1\times10^{-12}$ or less, or between $1\times10^{-9}$ and $1\times10^{-3}$, or between $1\times10^{-12}$ and $1\times10^{-9}$, or between $1\times10^{-9}$ and $1\times10^{-6}$, or between $1\times10^{-8}$ and $1\times10^{-6}$, or between $1\times10^{-6}$ and $1\times10^{-3}$, between $1\times10^{-6}$ and $1\times10^{-4}$, between $1\times10^{-6}$ and $1\times10^{-5}$, between $1\times10^{-5}$ and $1\times10^{-3}$, or between $1\times10^{-4}$ and $1\times10^{-3}$, or between $1.7\times10^{-11}$ and $1\times10^{-7}$, (observed 50% inhibition of TMA (or TMAO) formation from choline; mg/kg), in the assays described in EXAMPLE 6. In various embodiments, the compound of Formula (I) demonstrates an $IC_{50}$ of between $1\times10^{-11}$ and $1\times10^{-7}$, or between $1\times10^{-8}$ to $1\times10^{-3}$, or between $1.2\times10^{-6}$ to $2\times10^{-3}$, or between $1\times10^{-6}$ to $1\times10^{-4}$ (observed 50% inhibition of TMA formation from choline; mg/kg) as measured in the assays described in EXAMPLE 6.

The invention includes a method of inhibiting the conversion of choline to TMA in an individual which may comprise administering to an individual a composition comprising a compound set forth in Formula (I), as described previously. In certain embodiments, as described herein, an individual may be in need of reduced TMA levels, improvement of cardiovascular health, and the like. An individual may exhibit an elevated level of TMA or a metabolite thereof (e.g., TMAO, dimethylamine (DMA), or monomethylamine (MMA)) prior to administration. In various embodiments, an individual suffers from cardiovascular disease, ingests a diet high in choline, or exhibits one or more CVD risk factors (e.g., smoking, stress, high total cholesterol, high LDL cholesterol, low HDL cholesterol, age, hypertension, family history of CVD, obesity, prediabetes, diabetes, or the like).

A method of inhibiting the conversion of choline to TMA in vitro is also contemplated. For example, a method may comprise contacting a bacterium, such as a bacterium that is represented in the gut microflora, or a bacterial lysate that metabolizes choline to produce TMA with a compound of Formula (I), as described previously. In various embodiments, a bacterium may be selected from *Proteus mirabilis, Desulfovibrio alaskensis, Clostridium ljungdahlii, C. scindens, C. aldenense, C. aminobutyricum, Collinsella tanakaei, Anaerococcus vaginalis, Streptococcus dysgalactiae, Desultitobacterium hafniense, Klebsiella variicola, K. pneumonia, P. penneri, Eggerthella lenta, Edwardsiella tarda, Escherichia coli, E. fergussonii*, or a combination thereof. In certain embodiments the bacterium may be one which expresses the cutC/D gene cluster. The disclosure further provides a method of identifying a compound that inhibits TMA production. The method comprises contacting a bacterium, such as a bacterium that is part of the gut microflora, or a bacterial lysate that metabolizes choline to produce TMA with a candidate compound, such as a compound of Formula (I), and detecting TMA (or a metabolite thereof). In certain embodiments, the level of TMA (or metabolite thereof) produced by the bacterium in contact with the candidate compound is compared to (a) the level of TMA produced by a bacterium or lysate not contacted with a candidate compound or known TMA inhibitor or (b) the level of TMA produced by the bacterium prior to contact with the candidate compound. A reduction in the level of TMA produced by the bacterium or lysate indicates that the candidate compound inhibits conversion of choline to TMA.

A method of inhibiting the conversion of choline to TMA in vitro also is contemplated. The method comprises contacting bacteria or bacterial lysate with one or more compounds of Formula (I). In various embodiments, the bacteria comprise a single bacterial species or strain, or comprises a mixture of two or more (for example three, four, five, or more) different bacterial species or bacterial strains. Similarly, a bacterial lysate may be produced from a single bacterial species or strain, or a mixture of two or more (for example three, four, five, or more) different bacterial species or bacterial strains.

It will be appreciated that "inhibiting conversion of choline to TMA" does not require complete elimination of TMA production via choline metabolism. Any reduction in TMA formation from choline or a choline related metabolite as a precursor is contemplated, e.g., at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% reduction; and also including from about 1% to about 100%, from about 10% to about 90%, from about 20% to about 80%, from about 30% to about 70%, from about 40% to about 60%, and any combinations thereof.

In various embodiments, the inhibition of conversion of choline to TMA by the compounds of Formula (I) is not brought about by an antibiotic mechanism of action, for example it is not brought about by an antibacterial mechanism of action, or by a mechanism of action which reduces cell viability to 10% or lower, when compared to vehicle control.

In certain embodiments of the invention, the amount of compound needed to provide 50% inhibition of conversion of choline to TMA is less than the amount of compound that reduces cell viability to 10% or lower, when compared to vehicle control.

Any suitable method for measuring TMA in vitro or in vivo can be used in the context of the invention. TMA, metabolites of TMA (including TMAO, DMA, or MMA), stable isotopes of TMA (such as deuterium labeled TMA, such as d3-, d6-, or d9-TMA), stable isotopes of TMAO (such as deuterium labeled TMAO, such as d3-, d6-, or d9-TMAO), stable isotopes of DMA (such as deuterium labeled DMA, such as d3-, or d6-DMA), stable isotopes of MMA (such as deuterium labeled MMA, such as d3-MMA), or choline (including stable isotopes of choline, for example d9-choline) can be assessed quantitatively or qualitatively. Exemplary methods of detecting and quantifying TMA are described in, for example U.S. Pub. No. 2010/00285517, the disclosure of which is incorporated herein by reference in its entirety. For example, levels of TMA (or trimethylamine N-oxide (TMAO), DMA, or MMA) or choline are optionally measured via mass spectrometry, ultraviolet spectroscopy, or nuclear magnetic resonance spectroscopy. Mass spectrometers include an ionizing source (such as electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

In various embodiments, TMA or TMAO is measured in a biological sample from an individual. Biological samples include, but are not limited to, whole blood, plasma, serum, urine, feces, saliva, sweat, vaginal fluid, gingival crevicular fluid, or tissue. The sample may be collected using any clinically-acceptable practice and, if desired, diluted in an appropriate buffer solution, heparinized, concentrated, or fractionated. Any of a number of aqueous buffer solutions at physiological pH, such as phosphate, Tris, or the like, can be used. Acidified buffers also may be used. For example, the final pH after adding buffer to sample may optionally be between pH 1 and pH 6, or between pH 1.5 and pH 3.0.

In addition, levels of TMA (or a metabolite or stable isotope thereof) or choline in the biological sample may be compared to a control value. The control value utilized will depend on the embodiment of the invention. In certain embodiments, the control value may be the level of TMA or TMAO produced in the individual (or by the bacterium) prior to administration or exposure to a compound of Formula (I). In addition, the control value may be based on levels measured in comparable samples obtained from a reference group, such as a group of individuals from the general population, individuals diagnosed with a CVD or other TMA-associated condition, individuals not previously diagnosed with a TMA-associated condition, nonsmokers, and the like, who have not been exposed to a compound of Formula (I). Levels of TMA or TMAO or choline may be compared to a single control value or to a range of control values. An individual is optionally identified as having an enhanced level of TMA prior to administration by comparing the amount of TMA in a biological sample from the individual with a control value.

The invention further provides a method of improving cardiovascular health of an individual. The method comprises administering to the individual a composition comprising a compound set forth in Formula (I), as described above under the subheading "Compounds," in an amount effective to improve cardiovascular health. Cardiovascular health is assessed by testing arterial elasticity, blood pressure, ankle/brachial index, electrocardiogram, ventricular ultrasound, platelet function (for example platelet aggregation), and blood/urine tests to measure, for example cholesterol, albumin excretion, C-reactive protein, or plasma B-type peptide (BNP) concentration. In various aspects of the invention, administration of the compound of Formula (I) improves or maintains one or more of the assay outcomes within normal ranges. Normal ranges of outcomes of each test are known in the art. Improvement in cardiovascular health is, in some embodiments, marked by a reduction in circulating total cholesterol levels, reduction in circulating low density lipoproteins (LDLs), reduction in circulating triglycerides, or reduction in blood pressure.

The invention also includes a method of improving a condition associated with conversion of choline to TMA in an individual in need thereof. The method comprises administering to an individual a composition comprising a compound of Formula (I), in an amount effective to improve the condition. "Improving a condition" refers to any reduction in the severity or onset of symptoms associated with a disorder caused, at least in part, by TMA. One of ordinary skill in the art will appreciate that any degree of protection from, or amelioration of, a TMA-related disorder or symptom associated therewith is beneficial to an individual, such as a human. The quality of life of an individual is improved by reducing to any degree the severity of symptoms in an individual or delaying the appearance of symptoms. Accordingly, a method in one aspect is performed as soon as possible after it has been determined that an individual is at risk for developing a TMA-related disorder or as soon as possible after a TMA-related disorder is detected.

The condition associated with the conversion of choline to trimethylamine is, in various aspects of the invention, a cardiovascular disease, trimethylaminuria, reduced or impaired kidney function, kidney disease, chronic kidney disease, end-stage renal disease, trimethylaminuria, obesity or diabetes mellitus. The term "cardiovascular disease" (CVD) is used in the art in reference to conditions affecting the heart, heart valves, and vasculature (such as arteries and veins) of the body and encompasses diseases and conditions including, but not limited to, arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), cerebrovascular disease, adverse ventricular remodeling, ventricular systolic dysfunction, ventricular diastolic dysfunction, cardiac dysfunction, ventricular arrhythmia, and the like.

A condition may be atherosclerosis. Atherosclerosis involves the formation of atheromatous plaques that lead to narrowing ("stenosis") of the vasculature, which can ultimately lead to partial or complete occlusion or rupture (aneurism) of the vessel, heart failure, aortic dissection, and ischemic events such as myocardial infarction and stroke. In various non-limiting embodiments, an inventive method inhibits, reduces, or reverses (in whole or in part) the onset or progression of atherosclerosis (for example reducing or preventing hardening or thickening of the arteries, plaque formation, endothelium damage, or arterial inflammation).

A condition may be trimethylaminurina. Trimethylaminuria (TMAU) is a condition characterized by an inability of individuals to convert TMA to TMAO, wherein affected individuals may have a fish-like body odor present in their urine, sweat or breath. (Yamazaki et al. Life Sciences (2004) 74: 2739-2747). Such individuals may benefit from a reduction in metabolism of substrates including but not limited to choline, to TMA by bacteria in the gut. Individuals with TMAU or those wishing to reduce their levels of TMA and TMAO, may also consume activated charcoal or copper chlorophyllin, which act as sequestering agents, for example to make TMA unavailable to transfer into the blood stream of an individual. Such sequestering agents may adsorb TMA, which is then excreted from the digestive tract along with the sequestering agent.

The invention further provides the compounds of Formula (I) for use in inhibiting the conversion of choline to TMA in vivo or in vitro, for improving or maintaining a condition associated with the conversion of choline to TMA; and use of the compounds of Formula (I) for inhibiting the conversion of choline to TMA in vivo or in vitro, for improving or maintaining a condition associated with the conversion of choline to TMA. As described previously, the present invention is based, at least in part, on the discovery that compounds of Formula (I) inhibit choline metabolism by gut microbiota resulting in reduction in the formation of TMA and trimethylamine N-oxide (TMAO). The disclosure provides compositions and methods that for example inhibit the conversion of choline to TMA in vitro and in vivo, improve or maintain cardiovascular, cerebrovascular, and periphero-vascular health, and improve or prevent a condition associated with TMA and TMAO.

In various embodiments, administration of the compound of Formula (I) results in reduced TMA or TMAO levels, reduced total cholesterol levels, reduced LDL levels, increased HDL levels, reduced triglyceride levels, or normalized levels of other biomarkers associated with CVD (for example excreted albumin, C-reactive protein, or plasma B-type peptide (BNP)). In some embodiments, the compound of Formula (I) reduces the risk of cardiovascular disease, trimethylaminuria, reduced or impaired kidney function, kidney disease, chronic kidney disease, end-stage renal disease, trimethylaminuria, obesity, or diabetes mellitus, when administered to an individual.

Administration Regimens and Compositions

The amount of compound administered to the individual is sufficient to inhibit (in whole or in part) formation of TMA from choline. In various aspects of the disclosure, the amount improves cardiovascular health or achieves a beneficial biological response with respect to an unwanted condition associated with TMA (for instance the amount is sufficient to ameliorate, slow the progression, or prevent a condition (such as CVD)). The effect can be detected by, for example, an improvement in clinical condition, reduction in symptoms, or by any of the assays or clinical diagnostic tests described herein. The precise effective amount for an individual can depend upon the individual's body weight, size, and health; the nature and extent of the condition; and the compound or combination of agents selected for administration. In various aspects, the amount of compound administered to an individual is about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. An effective amount may be administered to an individual as a single deployment of compound or as a divided dose (such as a single dose administered in multiple subunits contemporaneously or close in time). An amount of compound may be delivered one, two, or three times a day; one, two, or three times a week; or one, two, three, or four times a month. The compound may be delivered as a prodrug, which is converted to an active drug in vitro or in vivo.

A composition comprising the compound is administered by any route that allows inhibition of choline conversion to TMA. A composition comprising the compound is, in various aspects of the invention, delivered to an individual parenterally (for example intravenously, intraperitoneally, intrapulmonary, subcutaneously or intramuscularly), intrathecally, topically, transdermally, rectally, orally, sublingually, nasally or by inhalation. In various embodiments, a compound or a composition comprising a compound is administered to the gastrointestinal tract via, such as by ingestion. Sustained release formulations may also be employed to achieve a controlled release of the compound when in contact with body fluids in the gastrointestinal tract. Sustained release formulations are known in the art, and typically include a polymer matrix of a biological degradable polymer, a water-soluble polymer, or a mixture of both, optionally with suitable surfactants.

The invention provides a composition comprising the compound of Formula (I) formulated with one or more physiologically acceptable excipients, carriers, stabilizers, tableting agents or diluents for use in the methods described herein. Excipients include, but are not limited to, carrier molecules that include large, slowly metabolized macromolecules such as proteins, polysaccharides, polylactic acids, polyglycolic acids, polymeric amino acids, amino acid copolymers, antioxidants (for example ascorbic acid), chelating agents (for example EDTA), carbohydrates (for example dextrin, hydroxyalkylcellulose, or hydroxyalkylmethylcellulose), liposomes, stearic acid, liquids (for example oils, water, saline, glycerol or ethanol), wetting or emulsifying agents, pH buffering substances, and the like.

Compositions, such as for parenteral or oral administration, are typically solids (for example, a lyophilized powder or cake), liquid solutions, emulsions or suspensions, while inhalable compositions for pulmonary administration are generally liquids or powders. Exemplary dosage forms include, but are not limited to, tablets, troches, lozenges, aqueous or oil suspensions, non-aqueous solutions, powders, dispersible powders or granules (including micronized particles or nanoparticles), emulsions, hard or soft capsules, hard or soft liquid-filled capsules, gelcaps, syrups, and elixirs. Solid dose compositions, for example tablets or liquid filled capsules may be uncoated or may be coated by known techniques including microencapsulation to delay disintegration and adsorption in the gastrointestinal tract. Solid dose compositions may be coated to target delivery to a specific region of the digestive tract. For example, the composition may be enteric coated to target delivery of the composition to the small intestine, the large intestine, or to the colon. Additional exemplary dosage forms may comprise coated microcapsules or coated microbeads in a suspension or liquid chassis. In some embodiments, the compound of Formula (I) is provided as a dietary (for example food or drink) supplement. Dietary supplements are orally dosed and typically comprise vitamins, minerals, herbs or other botanicals, amino acids, enzymes, organ tissues, tissues from glands, or metabolites. For example, a compound of Formula (I) may be provided as a food in the form of a bar.

In some embodiments, the compounds described herein may be formulated for oral administration in a lipid-based composition suitable for low solubility compounds. Lipid-based compositions can generally enhance the oral bioavailability of such compounds. As such, the composition comprises in some aspects, an amount of a compound described herein together with at least one excipient selected from medium chain fatty acids and propylene glycol esters thereof (e.g., propylene glycol esters of edible fatty acids, such as caprylic and capric fatty acids) and physiologically acceptable surfactants, such as polyoxyl 40 hydrogenated castor oil.

In some embodiments, the compounds described herein may be provided in a delayed release composition and are optionally released in a specific region of the digestive tract of an individual. For example, the composition may be provided such that the compounds are released from an orally dosed composition in the distal portion of the digestive tract such as the ileum or the colon. In certain embodiments, the delayed release composition releases the compounds at a specific pH, or at a range of pH for targeted delivery within the digestive tract of an individual. The compounds may be released, for example, between pH 6.0 and pH 9.0, between pH 6.5 and pH 8.0, between pH 6.5 and pH 7.5, between pH 7.0 and pH 7.5, or between pH 7.0 and pH 8.0.

A method of the invention may comprise administering a second agent to an individual. The term "second agent" merely serves to distinguish the agent from the compound of Formula (I) and is not meant to limit the number of additional agents used in a method or denote an order of administration. One or more second agents are optionally incorporated in the composition with the compound of Formula (I) administered concurrently but in separate dosage forms or administered separately in time.

Exemplary second agents include, but are not limited to, antimicrobials (such as antibiotics that kill bacteria in the gut); agents that improve intestinal motility (such as fiber or psyllium); agents that further reduce TMA levels in the gut including sequestering agents (such as activated charcoal, or copper chlorophyllin); agents that further reduce TMA levels or production of TMA metabolites; agents that improve one or more aspects of cardiovascular health, such as agents that normalize blood pressure, decrease vascular inflammation, reduce platelet activation, normalize lipid abnormalities; agents that promote the excretion of TMA from the body; or agents that bind TMA so that it cannot be converted to TMAO. In various embodiments, the second agent is selected from the group consisting of Omega 3 oil, salicylic acid (aspirin), dimethylbutanol, garlic oil, garlic extract, olive oil, hill oil, Co enzyme Q-10, a probiotic, a prebiotic, a dietary fiber, psyllium husk, bismuth salts, phytosterols, grape seed oil, green tea extract, vitamin D, an antioxidant (such as vitamin C and vitamin E), turmeric, curcumin, resveratrol, activated charcoal, or copper chlorophyllin. In certain embodiments, the composition comprises dimethylbutanol or inhibitors of the formation of TMA from precursors other than choline (for example betaine, phosphatidylcholine, crotonobetaine, or carnitine). Additional exemplary second agents are described in US 2017/0151208, US 2017/0151250, US 2017/0152222, or US 2018/0000754, which are incorporated here by reference.

A method of the disclosure may further comprise administration of one or more cardiovascular disease therapies. Examples of therapies include, but are not limited to, statins (e.g., Lipitor™ (atorvastatin), Pravachol™ (pravastatin), Zocor™ (simvastatin), Mevacor™ (lovastatin), and Lescol™ (fluvastatin)) or other agents that interfere with the activity of HMGCoA reductase, nicotinic acid (niacin, which lowers LDL cholesterol levels), fibrates (which lower blood triglyceride levels and include, for example Bezafibrate (such as Bezalip®), Ciprofibrate (such as Modalim®), Clofibrate, Gemfibrozil (such as Lopid®) and Fenofibrate (such as TriCor®)), bile acid resins (such as Cholestyramine, Colestipol (Colestid), and Cholsevelam (Welchol)), cholesterol absorption inhibitors (such as Ezetimibe (Zetia®, Ezetrol®, Ezemibe®)), phytosterols such as sitosterol (Take Control (Lipton)), sitostanol (Benechol), or stigmastanol), alginates and pectins, lecithin, and nutraceuticals (such as extract of green tea and other extracts that include polyphenols, particularly epigallocatechin gallate (EGCG), Cholest-Arrest™ (500 mg garlic and 200 mg lecithin). Cholestaway™ (700 mg Calcium carbonate, 170 mg magnesium oxidem 50 µg chromium picolinate), Cholest-Off™ (900 mg of plant sterols/stanols), Guggul Bolic (750 mg gugulipid (*Commiphora mukul* gum resin), and Kyolic® (600 mg aged garlic extract and 380 mg lecithin)).

In related variations of the preceding embodiments, a composition comprising a compound of Formula (I) described herein, alone or in combination with one or more second agents(s), may optionally be arranged in a kit or package or unit dose, such as a kit or package or unit dose permitting co-administration of multiple agents. In another aspect, the composition comprising a compound of Formula (I) and the one or more second agents are in admixture. In various embodiments, the component(s) of the kit or package or unit dose are packaged with instructions for administering the component(s) to an individual.

Other aspects and advantages of the present invention will be understood upon consideration of the following illustrative examples, which are not intended to be limiting in any way.

Structures of representative compounds of Formula (I) are set forth in TABLE 1. Pharmaceutically acceptable counterions may include, but are not limited to, chloride, bromide, or iodide, and salts and solvates thereof.

TABLE 1

| ID | Structure | SMILES | Compound Name |
|---|---|---|---|
| 1 | F-CH2CH2-N+(C)(C)-CH2Cl | C[N+](C)(CCF)CCl | N-(chloromethyl)-2-fluoro-N,N-dimethylethan-1-aminium |
| 2 | F-CH2CH2-N+(C)(C)-CH2I | C[N+](C)(CCF)CI | 2-fluoro-N-(iodomethyl)-N,N-dimethylethan-1-aminium |
| 3 | F-CH2CH2-N+(C)(C)-CH2F | C[N+](C)(CCF)CF | (2-fluoroethyl)(fluoromethyl)dimethyl-14-azane |
| 4 | Br-CH2-N+(C)(C)-CH2CH2F | C[N+](C)(CCF)CBr | N-(bromomethyl)-2-fluoro-N,N-dimethylethan-1-aminium |

EXAMPLES

Example 1: Syntheses of Compounds

All synthesis procedures were performed at room temperature (RT) and atmospheric pressure unless stated otherwise.

The following are representative compounds of Formula (I):

Example 1.1: Synthesis of N-(chloromethyl)-2-fluoro-N,N-dimethylethan-1-aminium chloride

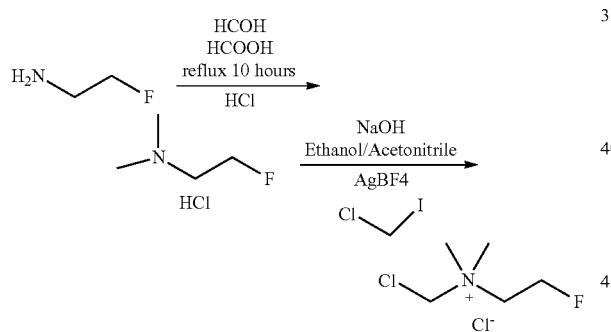

In a 250 mL round bottomed flask equipped with a stirring bar, an oil bath and a reflux condenser, 10 g 2-Fluoroethylamine hydrochloride (CAS 460-08-2) was added. 30 mL Formaldehyde solution (CAS 50-00-0, 37% in water) was added dropwise by glass pipette over 10 minutes. 40 mL Formic acid (CAS 64-18-6) was added dropwise by glass pipette over 10 minutes. The reaction mixture was refluxed at 110° C. for 10 hours. After cooling the reaction mixture to room temperature, 20 mL concentrated Hydrochloric acid (CAS 7647-01-0, 36.5-38.0%) was added. After rotary evaporation, the crude product (2-fluoro-N,N-dimethylethan-1-amine hydrochloric acid salt) was recrystallized in 2-propanol/diethyl ether. LC/MS: (ESI+) 92.

In a 250 mL round bottomed flask equipped with a stirring bar, 1 g 2-fluoro-N,N-dimethylethan-1-amine hydrochloric acid salt, 0.6 g sodium hydroxide (CAS 1310-73-2) and 40 mL ethanol/acetonitrile (1/1) were added. The reaction mixture was stirred at room temperature for 2 hours. The sodium chloride salt was removed using Chemrus disposable filter funnel. To the filtrated solution, 1.5 g Silver tetrafluoroborate (CAS 14104-20-2) and 2 mL Chloroiodomethane (CAS 593-71-5) were added. The reaction mixture was stirred at room temperature for 24 hours. The mixture was passed through a pre-packed Amberlite IRA Cl-form column (50 mL resin). The resin was further washed by methanol (100 mL). After rotary evaporation of the combined flow through, the oil-like product was further washed by ether (3×100 mL) and then dried overnight on house vacuum (5-10 mm Hg) to get 1.5 g final product. LC/MS: (ESI+) 140.

Example 1.2: Synthesis of 2-fluoro-N-(iodomethyl)-N,N-dimethylethan-1-aminium chloride

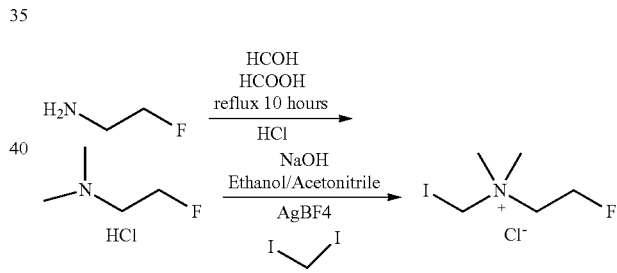

In a 250 mL round bottomed flask equipped with a stirring bar, an oil bath and a reflux condenser, 10 g 2-Fluoroethylamine hydrochloride (CAS 460-08-2) was added. 30 mL Formaldehyde solution (CAS 50-00-0, 37% in water) was added dropwise by glass pipette over 10 minutes. 40 mL Formic acid (CAS 64-18-6) was added dropwise by glass pipette over 10 minutes. The reaction mixture was refluxed at 110° C. for 10 hours. After cooling the reaction mixture to room temperature, 20 mL concentrated Hydrochloric acid (CAS 7647-01-0, 36.5-38.0%) was added. After rotary evaporation, the crude product (2-fluoro-N,N-dimethylethan-1-amine hydrochloric acid salt) was recrystallized in 2-propanol/diethyl ether. LC/MS: (ESI+) 92.

In a 250 mL round bottomed flask equipped with a stirring bar, 1 g 2-fluoro-N,N-dimethylethan-1-amine hydrochloric acid salt, 0.6 g sodium hydroxide (CAS 1310-73-2) and 40 mL ethanol/acetonitrile (1/1) were added. The reaction mixture was stirred at room temperature for 2 hours. The sodium chloride salt was removed using Chemrus disposable filter funnel. To the filtrated solution 1.5 g Silver tetrafluoroborate (CAS 14104-20-2) and 0.76 mL Diiodomethane (CAS 75-11-6) were added. The reaction mixture was stirred at room temperature for 24 hours. The mixture was passed through a pre-packed Amberlite IRA Cl-form column (50 mL resin). The resin was further washed by methanol (100 mL). After rotary evaporation of the combined flow through, the crude product was recrystallized in 2-propanol/diethyl ether and then dried overnight on house vacuum (5-10 mm Hg) to get 1 g final product. LC/MS: (ESI+) 232.

Example 1.3: Synthesis of 2-fluoro-N-(fluoromethyl)-N,N-dimethylethan-1-aminium chloride

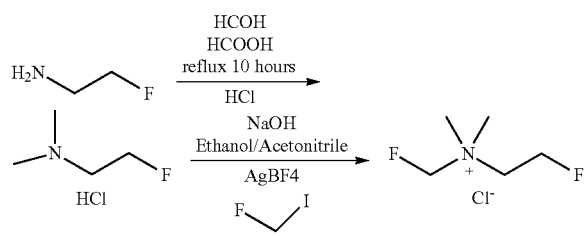

In a 250 mL round bottomed flask equipped with a stirring bar, an oil bath and a reflux condenser, 10 g 2-Fluoroethylamine hydrochloride (CAS 460-08-2) was added. 30 mL Formaldehyde solution (CAS 50-00-0, 37% in water) was added dropwise by glass pipette over 10 minutes. 40 mL Formic acid (CAS 64-18-6) was added dropwise by glass pipette over 10 minutes. The reaction mixture was refluxed at 110° C. for 10 hours. After cooling the reaction mixture to room temperature, 20 mL concentrated Hydrochloric acid (CAS 7647-01-0, 36.5-38.0%) was added. After rotary evaporation, the crude product (2-fluoro-N,N-dimethylethan-1-amine hydrochloric acid salt) was recrystallized in 2-propanol/diethyl ether. LC/MS: (ESI+) 92.

In a 250 mL round bottomed flask equipped with a stirring bar, 0.5 g 2-fluoro-N,N-dimethylethan-1-amine hydrochloric acid salt, 0.2 g sodium hydroxide (CAS 1310-73-2) and 40 mL ethanol/acetonitrile (1/1) were added. The reaction mixture was stirred at room temperature for 2 hours. The sodium chloride salt was removed using Chemrus disposable filter funnel. To the filtrated solution 1 g Silver tetrafluoroborate (CAS 14104-20-2) and 0.3 mL Fluoro(iodo) methane (CAS 373-53-5) were added. The reaction mixture was stirred at room temperature for 24 hours. The mixture was passed through a pre-packed Amberlite IRA Cl-form column (50 mL resin). The resin was further washed by methanol (100 mL). After rotary evaporation of the combined flow through, the crude product was recrystallized in 2-propanol/diethyl ether and then dried overnight on house vacuum (5-10 mm Hg) to get 0.5 g final product. LC/MS: (ESI+) 124.

Example 2: Assay for Identifying and Characterizing Compounds that Inhibit the Formation of TMA from Choline This example provides an exemplary assay for identifying and characterizing compounds that inhibit the formation of TMA from choline.

*Proteus mirabilis* 29906 (Pm) strain was grown aerobically overnight in 500 ml of Nutrient Broth media (3 g/L beef extract, 5 g/L Peptone; Difco #234000) at 37° C. with 250 rpm shaking. The biomass was pelleted by centrifugation at 6000×g for 12 minutes at 4° C. The cell pellet was suspended in 240 mL of ice-cold 1× Phosphate Buffered Saline ($Ca^{2+}$ and $Mg^{2+}$ free). Ninety micrograms of Lysozyme (Sigma # L6876 Lot # SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. A protein concentration of the centrifuged lysate supernatant was determined by a BCA Protein Assay Kit (Pierce #23225; Thermo Fisher Scientific Co., Waltham, Mass.) and protein concentration adjusted to 3 mg/ml with 1× Dulbecco's phosphate buffered saline (DPBS). The centrifuged supernatant lysate was aliquoted into 20 mL volumes and stored frozen at –80° C.

*Proteus mirabilis* 29906 (Pm) lysate was diluted to 1.5 mg/mL protein with 1×DPBS. Choline chloride (CC) (1M stock) was added to reach a final concentration of 2.5 mM choline chloride. The mixture was mixed using a vortex mixer for approximately 15 seconds and incubated at 37° C. for 22 hours. After incubation, 150 μL of CC-treated Pm lysate was dispensed into a deep-well plate (polypropylene, 2 mL volume, Corning Axygen catalogue # P-DW-20-C). Candidate $IC_{50}$ compounds from TABLE 1 and vehicle control (respective vehicle control of DMSO or water), or control compounds (IC50 control, 8-Quinolinol hemisulfate salt (Sigma Catalog #55100)) were added at a 1:100 dilution (e.g., 1.5 μL per well). The plates were agitated on a plate shaker for 1 minute. d9-choline chloride (1.5 μL of 5 mM) was added to all wells to reach a final d9-choline chloride concentration of 50 μM.

The plates were again agitated on a plate shaker for 1 minute and incubated at 37° C. for two hours. After incubation, 1.5 μL of formic acid was added to each well (final concentration=1% formic acid). The plates were agitated on a plate shaker for 1 minute and placed on ice. Cell lysate samples were spiked with stable isotope labeled internal standard (22.5 μL of 6 μg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 μL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography (HPLC) analysis on a Waters Atlantis HILIC Silica column, from Waters Corp., Milford, Mass., (2.1×50 mm, 3 μm particles) with an Atlantis Silica HILIC Sentry guard column, from Waters Corp., Milford, Mass., (100 Å, 3 μm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/×2) regression curve.

Example 2 Provides Exemplary Methods of Identifying and Quantitating TMA in A Sample, as Well as Screening Candidate Inhibitory Compounds $IC_{50}$ measurements for inhibition of conversion of choline to TMA, as outlined in EXAMPLE 2, for representative compounds of Formula (I), are set forth in TABLE 2.

TABLE 2

| ID | Name | SMILES | TMA Inhibition ($IC_{50}$, mol/L) |
|---|---|---|---|
| 1 | N-(chloromethyl)-2-fluoro-N,N-dimethylethan-1-aminium chloride | C[N+](C)(CCF)CCl•[Cl] | 2.700E−07 |
| 2 | 2-fluoro-N-(iodomethyl)-N,N-dimethylethan-1-aminium chloride | C[N+](C)(CCF)CI•[Cl] | 1.786E−07 |
| 3 | (2-fluoroethyl)(fluoromethyedimethyl-14-azane chloride | C[N+](C)(CCF)CF•[Cl] | 2.113E−07 |

Example 3 Polymicrobial Screening Method

Human fecal polymicrobial incubation with deuterium labeled choline compound screening method, including cell viability assay. All materials were pre-reduced in an anaerobic chamber for 24 hours before using in the experiments and experimental procedures were performed under anaerobic conditions (chamber purged with 85% nitrogen, 5% hydrogen, 10% carbon dioxide).

Human fecal samples were collected from a healthy male volunteer with no chronic illnesses, blood borne diseases or active infections. The volunteer had not received antibiotics within two months prior to donation and provided written informed consent. Samples were diluted to make a 20% (w/v) fecal slurry by resuspension of the feces in a media containing 3% (w/v) tryptic soy broth, 1% (w/v) trehalose, pH 7.3. The fecal slurry was homogenized and filtered by hand using a stomacher bag with an integrated 170 μm membrane. DMSO (5% (w/v)) was added to the filtered slurry and aliquots were stored in cryogenic vials at −80° C. until use. Frozen fecal slurries were diluted to 0.2% (w/v) with M9 media ($Na_2HPO_4$ (6 g/L), $KH_2PO_4$ (3 g/L), NaCl (0.5 g/L) with addition of 0.1 mM $CaCl_2$) and 1 mM $MgSO_4$) and dispensed (1 mL) into deep well 96-well plates. Diluted fecal slurries containing 50 μM d9-choline chloride and compounds in doses ranging from 500 μM to 3.81 nM were sealed and incubated at 37° C. with shaking. After 20 hours, an aliquot of the fecal polymicrobial community was analyzed for viability using PrestoBlue cell viability reagent (Thermo Fisher Scientific, USA) as described below. The reaction plates were subsequently centrifuged (4000× g at 4° C. for 12 min) to pellet fecal material and 150 μl aliquots were transferred and quenched with addition of formic acid to 1% (v/v). All fecal processing and polymicrobial assay steps were performed in an anaerobic environment. The products were determined by LC/MS/MS and $IC_{50}$ values were calculated as described previously for detection and analysis of TMA and d9-TMA in EXAMPLE 2. Inhibition of conversion of choline to TMA is calculated as $IC_{50}$ (mol/Liter)

For the PrestoBlue cell viability assay, a 6 μL aliquot of the fecal polymicrobial community assay was added to 84 μL M9 media in a black, clear bottom 96 well plate. To this was added 10 μL of PrestoBlue reagent, covered and shaken for 1 minute at 800 rpm. The plates were incubated at 37° C. for 30 minutes and fluorescence read following the manufacturer's instructions. Cell viability was calculated as % fluorescence compared to vehicle control (e.g. 1% DMSO).

EXAMPLE 3 provides exemplary methods of screening candidate inhibitory compounds for the conversion of choline to TMA and for calculation of cell viability.

Example 4 Preclinical Screening Method

Starting at day 0, mice (C57bl/6, ~19 g, 10 wk of age; n=5/group) were maintained in accordance with the NIH guidelines in a 12:12 hr light:dark cycle and provided with 1% Choline Added diet (Envigo custom formulation prepared, similar to Teklad Global Rodent Diet 2018) ad libitum. Concurrent with introduction of the diet, mice were gavaged once daily orally using a 1.5" 22 G ball-tip curved feeding needle to administer compound in 200 μl or less of water at one or multiple of the dose 0, 1.0, 3.1, 10, 31, 100 or 310 mg/kg/day. Urine was collected once daily in the morning. Animals were restrained by hand and bladder was expressed by gentle palpation of the pelvic region. Aliquots of 1-5 μl of urine were centrifuged at 1,300×g for 5 min in a 1.5 mL conical bottom tube with a snap top, to precipitate any potential cellular debris, and supernatants were transferred to a clean screw-cap tube with o-ring seal and stored at −80° C. until analysis. Sixty microliters or less of blood was collected at 20 hours post gavage, into a heparinized capillary tube. Blood was kept at 4° C., then spun using a centrifuge (5 min in centrifuge designed to capillary tubes) to separate plasma and hematocrit within 4 hours after collection. Plasma samples were stored at −80° C.

Measurements of Choline Metabolites:

For measurement of TMA in plasma, samples were acidified (10 mM HCl final) prior to storage at −80° C. TMAO and trimethylamine (TMA) and their d9-isotopologues were quantified using stable isotope dilution HPLC with on-line electrospray ionization tandem mass spectrometry (LC/EST/MS/MS) methods as described in (Wang Z, Klipfell E, Bennett B J, et al. (2011) Gut flora metabolism of phosphatidylcholine promotes cardiovascular disease. Nature 472: 57-63) using d4(1,1,2,2)-choline, d3(methyl)-TMAO, and d3(methyl)-TMA as internal standards. Concentrations of TMAO in urine were adjusted for urinary dilution by analysis of urine creatinine concentration. Samples were taken at different days during the studies and different doses were administered to avoid side effects at higher doses of some of the compounds.

EXAMPLE 4 provides exemplary methods of screening candidate inhibitory compounds for the conversion of choline to TMA. Inhibition is calculated as remaining plasma TMAO as a percentage of plasma TMAO in same day vehicle control.

Example 5: Additional In Vitro Assay for Identifying and Characterizing Compounds that Inhibit the Formation of TMA from Choline Ability of compounds to inhibit the conversion of choline to TMA in cell lysates or whole cells were determined using methods as described in Wang, Z, Roberts, A B, Buffa J A, et al. (2015) Non-lethal inhibition of gut microbial trimethylamine production for the treatment of atherosclerosis, Cell 163: 1585-1595. Briefly, efficacy was measured as IC50

(nM) by inhibition of conversion of choline to TMA metabolized by recombinant P. mirabilis Cut C/D lysate; recombinant D. alaskensis Cut C/D lysate, or whole cell wild-type P. mirabilis.

$IC_{50}$ measurements for inhibition of conversion of choline to TMA, as outlined in EXAMPLE 5, for representative compounds of Formula (I) are set forth in TABLE 3.

TABLE 3

| ID | Compound Name | IC50 (M) recombinant P. mirabilis Cut C/D lysate | IC50 (M) recombinant D. alaskensis Cut C/D lysate | EC50 (M) whole cell wild-type P. mirabilis |
|---|---|---|---|---|
| 1 | N-(chloromethyl)-2-fluoro-N,N-dimethylethan-1-aminium chloride | 6.90E−07 | 7.60E−07 | 8.70E−06 |
| 2 | 2-fluoro-N-(iodomethyl)-N,N-dimethylethan-1-aminium chloride | 2.40E−07 | 1.50E−07 | 6.70E−05 |
| 3 | (2-fluoroethyl)(fluoromethyl)dimethyl-14-azane chloride | 8.70E08 | 1.70E−07 | 7.20E−06 |

EXAMPLE 5 provides exemplary methods of identifying and quantitating TMA in a sample, as well as screening candidate inhibitory compounds. All compounds in TABLE 3 were found to inhibit the conversion of choline to TMA.

Example 6: Rapid Preclinical Method to Determine Compound Efficacy

Challenge: C57bl/6 female mice (8 wk of age ~20 g BW) were maintained in accordance with the NIH guidelines in a 12:12 hr light:dark cycle on normal chow diet were placed in a clean cage without food ~1 hr prior to gavage. Mice were given 2 mg d9-Choline+x mg/kg inhibitor (where x=0 to 310 mg/kg) in water by oral gavage using a 1.5" 22 G ball-tip curved feeding needle to administer compound in 200 μl of water. Food was returned after a 2 hr fast (1 hr after gavage administration). Blood (30 μL) was collected into a heparinized capillary tube at 2, 3 and 4 hours after gavage. Blood was kept at 4° C., then spun using a centrifuge (5 min in centrifuge designed to capillary tubes) to separate plasma and hematocrit within 4 hours after collection. Plasma samples were stored at −80° C. Concentration of d9 Choline, d9TMA and d9TMAO was measured by LC-MS/MS.

Flora Normalization: Twenty four hours post-gavage mice were placed in a clean cage and fecal material from conventional mice was spread in all the cages.

EXAMPLE 6 provides exemplary methods of screening candidate inhibitory compounds for the conversion of choline to TMA.

$EC_{50}$ measurements for inhibition of conversion of choline to TMA, as outlined in EXAMPLE 6, for representative compounds of Formula (I) are set forth in TABLE 4.

TABLE 4

Calculated $EC_{50}$ (mg/kg) compared to Vehicle Control, as described in EXAMPLE 6

| ID | Compound Name | $EC_{50}$ (mg/kg) | Time |
|---|---|---|---|
| 1 | N-(chloromethyl)-2-fluoro-N,N-dimethylethan-1-aminium chloride | 3.10 | 3 hr |
| 2 | 2-fluoro-N-(iodomethyl)-N,N-dimethylethan-1-aminium chloride | 15.40 | 3 hr |
| 3 | (2-fluoroethyl)(fluoromethyedimethyl-14-azane chloride | 1.10 | 3 hr |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a physiologically acceptable carrier and a compound of Formula (I):

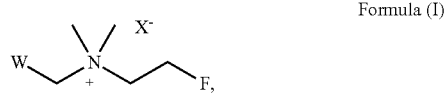

Formula (I)

wherein:
W is selected from F, Cl, Br or I;
$X^-$ is a pharmaceutically acceptable anion,
and including any acceptable salts or solvates thereof.

2. The composition of claim 1 wherein the compound is selected from the group consisting of: N-(chloromethyl)-2-fluoro-N,N-dimethylethan-1-aminium chloride, 2-fluoro-N-(iodomethyl)-N,N-dimethylethan-1-aminium chloride, (2-fluoroethyl)(fluoromethyl)dimethyl-14-azane chloride and N-(bromomethyl)-2-fluoro-N,N-dimethylethan-1-aminium chloride, and including any acceptable salts or solvates thereof.

3. The composition of claim 1 wherein W is F, $X^-$ is selected from $Cl^-$, $Br^-$ or $I^-$,
including any acceptable salts or solvates thereof.

4. A method of inhibiting the conversion of choline to trimethylamine (TMA) and reducing TMAO level in an individual comprising administering to the individual a composition comprising a compound set forth in Formula (I):

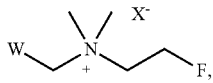

wherein:
W is selected from F, Cl, Br or I;
X⁻ is a pharmaceutically acceptable anion,
and including any acceptable salts or solvates thereof;
wherein the compound is administered in an amount effective to inhibit formation of trimethylamine (TMA) from choline in the individual.

5. The method of claim 4 wherein
W is F, X⁻ is selected from Cl⁻, Br⁻ or I⁻, and including any acceptable salts or solvates thereof.

6. The method of claim 4 wherein the compound is selected from the group consisting of: N-(chloromethyl)-2-fluoro-N,N-dimethylethan-1-aminium chloride, 2-fluoro-N-(iodomethyl)-N,N-dimethylethan-1-aminium chloride, (2-fluoroethyl)(fluoromethyl)dimethyl-14-azane chloride and N-(bromomethyl)-2-fluoro-N,N-dimethylethan-1-aminium chloride, and including any acceptable salts or solvates thereof.

7. The method of claim 4 comprising administering to the individual a second agent selected from the group consisting of Omega 3 oil, salicylic acid, dimethylbutanol, garlic oil, olive oil, krill oil, Co enzyme Q-10, a probiotic, a prebiotic, dietary fiber, psyllium husk, bismuth salts, phytosterols, grape seed oil, green tea extract, vitamin D, an antioxidant, turmeric, curcumin, and resveratrol.

8. The method of claim 4, comprising administering the compound to an individual having an elevated level of TMAO in blood, plasma, serum, or urine, and combinations thereof.

* * * * *